United States Patent [19]

Khan

[11] Patent Number: 5,294,593
[45] Date of Patent: Mar. 15, 1994

[54] INDUCING DORMANCY IN NON DORMANT SEEDS

[75] Inventor: Anwar A. Khan, Geneva, N.Y.

[73] Assignee: Cornell Research Foundation, Inc., Ithaca, N.Y.

[21] Appl. No.: 882,962

[22] Filed: May 14, 1992

[51] Int. Cl.$^5$ ............... A01N 43/54; A01N 43/64; A01N 43/647
[52] U.S. Cl. ................... 504/100; 504/239; 504/261; 504/272; 504/274; 504/248; 504/319; 504/345; 47/57.6
[58] Field of Search .............. 71/92, 65; 504/100, 504/272, 274, 261, 234, 248

[56] References Cited

U.S. PATENT DOCUMENTS

| | | | |
|---|---|---|---|
| 3,803,761 | 4/1974 | Watts et al. | 47/57.6 |
| 4,189,434 | 2/1980 | Platz et al. | 71/76 |
| 4,578,483 | 3/1986 | Mabelis | 549/297 |
| 4,604,129 | 8/1986 | Schott et al. | 71/76 |
| 4,637,828 | 4/1987 | Schulze et al. | 71/76 |
| 4,664,697 | 5/1987 | Kaufmann, Jr. | 71/92 |
| 4,978,555 | 12/1990 | Bley | 426/627 |
| 5,073,187 | 12/1991 | Elliot | 71/92 |

OTHER PUBLICATIONS

CA 110(13):110065x, Yang et al, "Effect of Tetcyclacis and Chlormequat Chloride Applied to Seed . . . ", Plant Growth Regul. 7(4), 289–301 (1988) (Abstract included).
Black, M., Symp. Soc. Exp. Biol. 23: 193–217, 1969.
DeGreef, J. A., et al, In: Recent Advances in the Development and Germination of Seeds, R. B. Taylorson, ed., pp. 241–260, NATO ASI Series, Plenum Press, N.Y., 1989.
Khan, A. A., In: The Physiology and Biochemistry of Seed Dormancy and Germination, A. A. Khan, ed., pp. 29–50, Elsevier/North-Holland Biomedical Press, Amsterdam, 1977.
Rethy, R., et al, Plant Physiol., 83, 126–130 (1987).
Van Der Woude, W. J., Photochem and Photobiol, 42, 655–661, 1985.
Van Der Woude, W. J., In: Recent Advances in the Development and Germination of Seeds, R. B. Taylorson, ed., pp. 181–189, NATO ASI Series, Plenum Press, N.Y. 1989.
Wareing, P. F., et al, Annu. Rev. Plant Physiol., 22: 261–288 (1971).
Gardner, G., J. Plant Growth Regul, 2:159–163 (1983).
Hilhorst, H. W. M., et al, Plant Physiol., 86, 591–597 (1988).
Karssen, C. M., et al, Annals of Botany, 63, 71–80 (1989).
Khan, A. A., Science, 171, 853–859, 5 Mar. 1971.

*Primary Examiner*—Glennon H. Hollrah
*Assistant Examiner*—B. Bembenick

[57] ABSTRACT

Dormant seeds, e.g., of lettuce, tomatoes, peppers, carrots, onions, impatiens and primrose, are produced by soaking non-dormant seeds in a solution of gibberellin synthesis inhibitor, preferably tetcyclacis, preferably in the dark at 25° C. to 350° C. for at least 24 hours, washing to remove the inhibitor and drying to original seed weight. The dormancy can be released by application of a gibberellin, and in some cases by moist chilling, or exposure to light at 25° C. to 35° C.

23 Claims, No Drawings

INDUCING DORMANCY IN NON DORMANT SEEDS

This invention was made at least in part with Federal funds appropriated under The Hatch Act and is Project No. NYG 632488; thus the Government has certain rights in the invention.

TECHNICAL FIELD

This invention is directed to inducing releasable dormancy in non-dormant plant seeds for which gibberellin synthesis is necessary for germination.

BACKGROUND OF THE INVENTION

The seeds of many plants are non-dormant, i.e., they readily germinate in light and/or darkness. This limits the way in which these seeds may be utilized. In other words, they must be planted at certain times of the year or a certain time before the desired maturity date.

Inducing releasable dormancy in these seeds allows the use of different planting strategies than now are used. This is especially important in the bedding plant industry. For example, imparting releasable dormancy to seeds allows planting the seeds in containers which are kept at room temperature and releasing the dormancy upon consumer demands or in accordance with a schedule set up by need. Furthermore, inducing releasable dormancy allows flexibility in field planting and is of importance especially in those areas where conditions are not conducive to spring planting (e.g., soft or muddy soil) since seeds imparted with releasable induced dormancy can be planted in the fall for germination in the spring.

SUMMARY OF THE INVENTION

It is an object herein to provide a method of inducing releasable dormancy in non-dormant plant seeds for which gibberellin synthesis is necessary for germination, which provides the advantages of different planting strategies from normal that are described above.

In one embodiment the method, herein comprises the steps of (a) soaking non-dormant plant seeds for which gibberellin synthesis is necessary for germination in a solution of a gibberellin synthesis inhibitor of concentration such and at a temperature such and for a time such as to induce dormancy therein, (b) washing to remove the gibberellin synthesis inhibitor from the seeds, and (c) drying the seeds to their weight prior to soaking in step (a).

A second embodiment herein is directed to a method of postponing the germinability of plant seeds for which gibberellin synthesis is necessary for germination and comprises inducing releasable dormancy in non-dormant plant seeds for which gibberellin synthesis is necessary for germination by the method of the aforestated first embodiment and after a desired interval, for example 1 day to 6 months, releasing the induced dormancy.

The expression "inducing releasable dormancy" is used herein to mean imparting to seeds dormancy, i.e., the inability to germinate under conditions which permitted their germination prior to induction of releasable dormancy, e.g., the inability to germinate in water at 25° C. in darkness, which is released or broken or reversed by treatment or conditions as described hereinafter to restore to the seeds the ability to germinate under conditions which permitted their germination prior to said inducing.

The term "light" when used without a preceding modifier includes white light, daylight, fluorescent light and red light (660 nm). Green safe light and darkness can be used interchangeably herein.

DETAILED DESCRIPTION

We turn now to the invention in detail.

The seeds that are subject to treatment in the invention herein are those for which gibberellin synthesis is necessary for germination and are for plants which are cultivated, e.g., seeds for vegetables such as lettuce, tomato, pepper, carrot, onion, celery, parsnip, endive, chicory, radish, leek, eggplant, potato and sweet potato; fruits such as Virginia strawberry (*Fragaria virginiana*); grasses such as Kentucky blue grass (*Poa pratensis*); trees and shrubs such as pine (*Pinus sylvestris*) and mullein (*Verbascum thapsus*); flowers such as impatients (*Impatiens*), primrose (*Primula spp.*) and evening primrose (*Oenothera spp.*); and other crops, such as tobacco (*Nicotiana tabaccum*).

The gibberellin synthesis inhibitors are those that interrupt or interfere with the gibberellin biosynthesis pathway. This pathway involves conversion of mevalonic acid (1) to isopdntenyl pyrophosphate (2), conversion of (2) to geranyl pyrophospate (3), conversion of (3) to farnesyl pyrophosphate (4), conversion of (4) to geranylgeranyl pyrophosphate (5), conversion of (5) to copalyl pyrophosphate (6), conversion of (6) to ent-kaurene(7), conversion of (7) to ant-kaurenol (8), conversion of (8) to ent-kaurenal (9), conversion of (9) to ent-kaurenoic acid (10), conversion of (10) to ent-7a-OH-kaurenoic acid (11), conversion of (11) to gibberellin $A_{12}$-aldehyde (12), conversion of (12) to gibberellin $A_{44}$ (open lactone) (13), conversion of (13) to gibberellin $A_{19}$ (14), conversion of (14) to gibberellin $A_{20}$ (15), conversion of (15) to gibberellin $A_1$ (16), conversion of (16) to gibberellin $A_8$ (17). The gibberellin synthesis inhibitors include N-containing heterocycles which inhibit the oxidative steps leading from entkaurene to ent-kaurenoic acid, onium compounds which inhibit gibberellin synthesis pathway steps before ent-kaurene (i.e., conversion of (5) to (6) and conversion of (6) to (7)), and cyclohexanetriones which inhibit gibberellin synthesis pathway steps after gibberellin $A_{12}$-aldehyde. The N-containing 15. heterocycles are preferred and include pyrimidines such as α-cyclopropyl-α-(4-methoxyphenyl)-5-pyrimidinemethanol (a and flurprimidol; norbornanodiazetins such as 5-(4-chlorophenyl)-3,4,5,9,10-pentaazatetracyclo [5.4.10$^{2,6}$.O$^{8,11}$-dodeca-3,9-diene (tetcyclacis); and triazoles such as 1-(4-chlorophenyl)-4,4-dimethyl-2-dimethyl-2-(1H-1,2,4-triazole-1-yl)-pentan-3-ol(paclobutrazol), uniconazol, triapenthenol, 1-phenoxy-3(1H-1,2,4-triazol-1-yl)-4-hydroxy-5,5-dimethylhexane (BAS 111 ... W), inabenfide, and 1-(2,6-diethylphenyl-imidazole-5-carboxamide (HOE 074 784). The onium compounds include (2-chloroethyl)trimethylammonium chloride) (chlormequat chloride or CCC), mepiquat chloride, 2 1 -isopropyl-4'-(trimethylammonium chloride)-5'-methylphenyl piperidine carboxylate (AMO-1618), and chlorophonium chloride. The cyclohexanetriones include 4-(cyclopropyl-a-hydroxymethylene) -3,5-dioxocyclohexanecarboxylic acid ethylester (cimectacarb), prohexadione calcium and 4-(n-propyl-α-hydroxymethylene)-3,5-dioxocyclohexanecarboxylic acid ethyl ester (LAB 198 999). Tetcyclacis and paclobutrazol are preferred with tetcyclacis being most preferred.

We turn now to the conditions of step (a) described above. The gibberellin synthesis inhibitor solution typically is an aqueous solution and the concentration of gibberellin synthesis inhibitor therein ranges from 1μM to 1μM, preferably from 5μM to 200μM. Alternatively, organic solvents such as acetone or dichloromethane can be used to permeate gibberellin biosynthesis inhibitors into seeds; after a 1 to 2 hour soak, the organic solvent is evaporated by vacuum desiccation or by forced air and the dried seeds with permeated gibberellin inhibitor can then be soaked with water to induce dormancy. The time for the aqueous soaking in step (a) should exceed 15 hours and usually a 24 hour soak is sufficient to induce dormancy. The upper limit for the time of aqueous soaking is uncritical and it is preferred to utilize the minimum time sufficient to induce dormancy. However, if desired, aqueous soaking may be carried out for a period of up to 7 days or more. The temperature utilized during aqueous soaking in step (a) typically ranges from about 25° C. to 35° C. with higher temperatures being used with lower concentrations of inhibitor and with lower temperatures being used with higher concentrations of inhibitor. The aqueous soaking in step (a) is preferably carried out in the dark although it can be carried out under light to obtain a lesser degree of induced dormancy or with more stringent concentration and temperature conditions or for seeds such as tomato or pepper where light is not effective in releasing dormancy.

The washing step (b) is carried out with aqueous washing liquid, typically water, and is such as to remove the gibberellin synthesis inhibitor of step (a) from the seeds. Typically, an excess of washing liquid is utilized. This washing should be carried out under safe green light or total darkness for seeds where dormancy is released by light such as lettuce seeds but can be carried out under light or darkness for seeds where light is ineffective in releasing dormancy such as tomato or pepper.

The drying step (c) is carried out under conditions which do not break (release) dormancy to restore the seeds to their weight (moisture content) prior to the soaking. This is appropriately carried out by drying in air (or forced air from a fan), e.g., at 25° C. to 35° C. for 30 minutes to 5 hours, preferably from 1 to 2 hours, under safe green light or total darkness for seeds where dormancy is released by light such as lettuce seeds and in light or darkness for seeds where light is ineffective in releasing dormancy such as tomato or pepper.

The seeds so processed can be stored for several months without loss of dormancy or responsiveness to dormancy releasing procedures.

Typically the inducing of dormancy is denoted by failure to germinate in water at 25° C. in darkness.

We now turn to the release of the induced dormancy, that is to the restoration of the non-dormant state. The methods for this all involve fostering the production of or otherwise supplying gibberallins.

One method for releasing dormancy involves soaking in water in light at 25° C. to 35° C. for a time period sufficient to release dormancy and foster germination, e.g., 1 to 10 days.

A second method of releasing dormancy is by the application to the seeds of a dormancy releasing amount of a gibberellin for a time sufficient to release dormancy and foster germination, 6.9, 1 to 10 days in light or darkness. A very suitable gibberellin this purpose consists of from 40% to 60% by weight gibberellin $A_4$ and from 40% to 60% by weight gibberellin $A_7$ and a gibberellin composition meeting these limits contains by weight 45.5% gibberellin $A_4$, 47.1% gibberellin $A_7$ and 7.5% inactive ingredient and is referred to hereinafter as gibberellin $A_{4+7}$. A suitable gibberellin which is somewhat less effective than gibberellin $A_{4+7}$ is gibberellin $A_3$. Other gibberellins work to varying degrees in releasing dormancy. Typically the gibberellin is applied as a 5μM to 1mM aqueous solution. Germination is readily effected by soaking seeds in gibberellin solution on a blotter in petri plates or on other synthetic or natural media saturated with gibberellin solution.

A third method of releasing dormancy involves chilling the dormant seeds, e.g., at 2 to 10° C., preferably at 5° C., with moisture present, e.g., for 4 to 40 days. This third method can be carried out by taking active steps, e.g., by soaking the seeds on a water soaked blotter or other moist media, e.g., for 4 to 15 days at 2 to 1DOC, preferably 5° C., in dark, as indicated by germination of seeds thus treated in water in the dark at 25° C. For example, 50 seeds can be moist chilled in a 5 cm plate lined with two layers of Whatman No. 1 filter paper moistened with 3ml water. This third method can also be carried out by planting in a moist peat-lite mix (from admixture of 10 cubic feet of sphagnum peat moss, 4 cubic feet of vermiculite, 5 lbs. of ground dolmitic limestone, I lb. of calcium nitrate, 0.5 lb. of iron sulfate, 3 ounces of fritted trace elements and 1 quart wetting agent) and maintaining moist conditions for 30 days at 2° to 10° C., preferably 5° C., as indicated by the emergence of normal healthy seedlings on transfer to 25° C. For example, seeds can be planted at 30 to 50 seeds in a row in rows 1 cm deep in thoroughly wetted peat-lite contained in 10×12×4 inches plastic boxes with the boxes being kept covered to prevent moisture evaporation during chilling. This third method can also be carried out by planting the seeds at a time such that weather conditions will supply the chilling, e.g., by planting in the fall in a northern climate for germination in the spring.

Release of dormancy and germination are two distinct processes or events. Dormancy can be released without a seed showing any sign of germination (usually radicle protrusion). Unlike germination, dormancy release is reversible. Dormancy can be released but if temperature is not suitable for germination, seeds will not germinate. This is quite common under field conditions. Many crop seeds are dormant in autumn or at harvest time when they fall to the ground and lose their dormancy in the soil by winter chilling but do not germinate until the following spring or summer when the soil temperature (20° to 30° C.) and soil water potential (not too dry) is right for germination or seedling emergence.

After dormancy is released herein, the seeds have the ability to germinate under the conditions which permitted their germination prior to the inducing of dormancy herein.

The invention is illustrated by the following specific examples.

EXAMPLE I

Dormancy was induced in lettuce seeds by soaking them in darkness for 24 hours at 25° C. in aqueous solutions of 50μM and 100μM tetcyclacis, and then washing was carried out with 200 ml water under suction in a sintered glass funnel and drying was carried out at 25° C. for 1 to 2 hours under safe green light by is forced air generated with a fan to original moisture content. Then, the seeds were maintained in water in light and darkness for 10 days with the results set forth below in Table 1 wherein "cvs." stands for cultivars and "UNTI stands for untreated with tetcyclacis.

TABLE 1

| Lettuce cvs. | Light germination (%) | | | Dark germination (%) | | |
|---|---|---|---|---|---|---|
| | UNT | 50 μM | 100 μM | UNT | 50 μM | 100 μM |
| Grand Rapids | 98 | 61 | 1 | 24 | 0 | 0 |
| Emperor | 98 | 100 | 99 | 98 | 22 | 10 |
| Ithaca | 99 | 99 | 96 | 98 | 32 | 14 |
| Garnet | 98 | 5 | 2 | 0 | 0 | 0 |
| Montello | 98 | 96 | 94 | 96 | 23 | 6 |
| Empress | 99 | 99 | 97 | 99 | 9 | 4 |
| Mesa 659 | 96 | 15 | 1 | 99 | 0 | 0 |

EXAMPLE II

Dormancy was induced in lettuce seeds by soaking them in aqueous solution of tetcyclacis of concentration in μM as set forth in parentheses in Table 2 below for 24 hour at 25° C. in darkness and then washing and drying was carried out in the same way as in Example I. The resulting seeds were soaked at 25° C. in 5 cm petri plates lined with two layers of Whatman NO. 1 filter paper moistened with 3 ml of water or 1 mM aqueous gibberellin $A_{4+7}$ (the water or aqueous gibberellin was applied to the filter paper by pipetting). Germination was recorded after 10 days. The results are set forth in Table 2 below where "$GA_{4+7}$" stands for gibberellin $A_{4+7}$.

TABLE 2

| Lettuce cvs. | Dark Germination (%) | |
|---|---|---|
| | $-GA_{4+7}$ | $+GA_{4+7}$ |
| Grand Rapids (50) | 0 | 98 |
| Emperor (100) | 6 | 98 |
| Montello (50) | 7 | 97 |
| Empress (100) | 1 | 46 |
| Garnet (20) | 1 | 10 |
| Ithaca (100) | 12 | 96 |

EXAMPLE III

Dormancy was induced in lettuce seeds by soaking them in aqueous solution of tetcyclacis of concentration in μM as set forth in parentheses in Table 3 below for 24 hours at 25° C. in darkness, and then washing and drying was carried out in the same way as in Example I. The resulting seeds (50 seeds/plate) were chilled in the dark in the presence of moisture at 5° C. in 5 cm petri plates lined with two layers of Whatman No. 1 filter paper in 3 ml water, for 10 days. The plates containing the seeds (in dark plastic bags) were transferred from a 5° C. room to a 25° C. room for germination in the dark. The seeds were then maintained for 7 days at 25° C. in darkness. Germination was monitored in safe green light. The results are set forth in Table 3 below in which "cvs." stands for cultivars and "TCY" stands for tetcyclacis.

TABLE 3

| Lettuce cvs. | 0 Day chilled | | 10 Day Chilled | |
|---|---|---|---|---|
| | −TCY | +TCY | −TCY | +TCY |
| | % Germination | | | |
| Garnet | 0 | 0 (5) | 98 | 80 (5) |
| Ithaca | 98 | 14 (100) | 99 | 88 (100) |
| Empress | 99 | 4 (100) | 99 | 96 (100) |
| Grand Rapids | 24 | 0 (5) | 85 | 35 (5) |
| Emperor | 98 | 22 (100) | 98 | 60 (100) |

TABLE 3-continued

| Lettuce cvs. | 0 Day chilled | | 10 Day Chilled | |
|---|---|---|---|---|
| | −TCY | +TCY | −TCY | +TCY |
| Montello | 95 | 6 (50) | 98 | 71 (50) |
| Mesa 659 | 98 | 0 (100) | 99 | 92 (100) |

EXAMPLE IV

Dormancy was induced in Mesa 659 lettuce seeds by soaking them in aqueous solution of tetcyclacis of concentration in μM as set forth in parentheses in Table 4 below for 24 hours at 25° C. in light (denoted "L" in Table 4 below) or in darkness (denoted "D" in Table 4 below), and then washing and drying was carried out in the same way as in Example I. The resulting seeds were planted in a thoroughly wetted peat-lite mix (of the type specifically described above) in plastic trays and the trays were transferred to a 5° C. dark room. After periods in the 5° C. dark room as set forth in Table 4 below, the trays were transferred to 25° C. in light and seedling emergence was recorded daily until emergence was completed. The results are set forth in Table 4 below in which "UNT" stands for untreated with tetcyclacis and "TCY" stands for tetcyclacis.

TABLE 4

| TCY (μM) | Moist-chilling at 5° C. (days) | | | |
|---|---|---|---|---|
| | 0 | 8 | 15 | 30 |
| | % Emergence at 25° C. | | | |
| UNT | 76 | 96 | 97 | 97 |
| 10 (L) | 36 | 50 | 67 | 82 |
| 50 (L) | 3 | 8 | 23 | 39 |
| 100 (L) | 0 | 2 | 18 | 13 |
| 5 (D) | 10 | 39 | 72 | 80 |
| 10 (D) | 0 | 45 | 62 | 67 |
| 50 (D) | 0 | 4 | 11 | 9 |

EXAMPLE V

Dormancy was induced in 93% and 83% of Empress and Mesa 659 lettuce seeds by soaking them in aqueous solution of 100μM paclobutrazol for 24 hours at 25° C. in darkness and then washing and drying was carried out in the same way as in Example I. The dormancy was reversed by maintaining the seeds in water in light at 25° C. for 10 days, by maintaining them at 25° C. for 10 days in darkness in the presence of 1mM aqueous gibberellin $A_{4+7}$ and by maintaining them (50 seeds/petri plate lined with two layers of Whatman No. 1 filter paper soaked with 3 ml water) at 5° C. for 10 days.

EXAMPLE VI

Dormancy was induced in various pepper (*Capsicum Annuum L.*) cultivars by soaking them in aqueous solution of tetcyclacis for 24 hours at 25° C. to 30° C. in light or darkness. Concentrations of tetcyclacis used for the six cultivars was as follows: Yolo Wonder, 100–170μM; Cayenne, 150–200μM; California wonder, 200–300μM; El Paso, 600μM; and Anaheim, 600μM. Washing was carried out in the same way as in Example I and the washed seeds were air dried in light to original moisture content (seed weight). Dormancy was released by treatment with 10μM aqueous gibberellin $A_{4+7}$. Light and moist chilling were ineffective to release dormancy.

EXAMPLE VII

Dormancy was induced in Jackpot and Super Marmande tomato cultivars by soaking them in aqueous solutions of tetcyclacis for 24 hours at 25° C. to 30° C. in light or darkness. Concentrations of tetcyclacis used for the two cultivars were 100–200μM. Washing and drying in light or darkness and otherwise as in Example I produces dormant dry seeds. Dormancy is released by treatment with 10μM to 1mM aqueous gibberellin $A_{4+7}$ in both cultivars but not by light or moist chilling.

EXAMPLE VIII

Dormancy was induced in carrot seeds by soaking them in aqueous solutions of tetcyclacis for 24 hours at 25° C. in darkness. Concentrations of tetcyclacis used were 10 to 100μM. Seeds became completely dormant at tetcyclacis concentrations of 10μM and above. Washing and drying as in Example I produces dormant dry seeds. Dormancy is released by treatment with 1mM aqueous gibberellin $A_{4+7}$ but not by light or moist chilling.

EXAMPLE IX

Dormancy was induced in onion seeds by soaking in 10μM aqueous tetcyclacis for 24 hours at 25° C. in darkness. Washing and drying as in Example I produces dormant dry seeds. Dormancy was released by treatment with 1mM aqueous gibberellin $A_{4+7}$.

EXAMPLE X

Dormancy was induced in impatients seeds by soaking in 50μM aqueous solution of tetcyclacis for 24 hours at 25° C. in darkness. Washing and drying as in Example I produces dormant seeds. Dormancy was released by treatment with 1mM aqueous gibberellin $A_{4+7}$.

EXAMPLE XI

Dormancy was induced in primrose seeds by soaking in 5μM aqueous solution of tetcyclacis for 24 hours at 25° C. in light or darkness. Washing and drying as in Example I produces dormant dry seeds. Dormancy was released with 1mM aqueous gibberellin $A_{4+7}$.

In all moist-chilling and germination studies in the above examples, where petri plates were used, the plates were kept inside a plastic box of dimensions 12×10×4 inches to prevent evaporation of water or soak solution.

Many variations of inventive embodiments well be obvious to those skilled in the art. Thus, the invention is defined by the claims.

What is claimed is:

1. A method of inducing releasable dormancy in non-dormant plant seeds for which gibberellin synthesis is necessary for germination, comprising the steps of
   (a) soaking said seeds in a solution of a gibberellin synthesis inhibitor of concentration such and at a temperature such and for a time such as to induce dormancy therein, said gibberellin synthesis inhibitor being one that inhibits the gibberellin biosynthesis pathway from ent-kaurene to ent-kaurenoic acid,
   (b) washing to remove the gibberellin synthesis inhibitor from the seeds, and
   (c) drying the seeds to their weight prior to soaking in step (a).

2. The method of claim 1 wherein the gibberellin synthesis inhibitor is a N-containing heterocycle.

3. The method of claim 2 wherein the gibberellin synthesis inhibitor is selected from the group consisting of norbornanodiazetins and triazoles.

4. The method of claim 2 wherein the gibberellin synthesis inhibitor is a pyrimidine.

5. The method of claim 4 wherein the gibberellin synthesis inhibitor is selected from the group consisting of ancymidol and flurprimidol.

6. The method of claim 1 wherein the concentration of gibberellin synthesis inhibitor in step (a) ranges from about 5μM to 200 μM, wherein the temperature in step (a) ranges from about 25° C. to 35° C. and wherein the time for step (a) is at least about 15 hours.

7. The method of claim 6 wherein said time is at least about 24 hours.

8. The method of claim 6 wherein the plant seeds are selected from the group consisting of lettuce, tomato, pepper, carrot, onion, impatients and primrose seeds.

9. A method for postponing the germinability of plant seeds for which gibberellin synthesis is necessary, said method comprising the steps of inducing dormancy in said seeds by the method of claim 1, and after a desired interval releasing the induced dormancy.

10. The method of claim 9 wherein the induced dormancy is released by soaking the seeds in water in light at about 25° C. to 35° C. for a time sufficient to release the induced dormancy.

11. The method of claim 9 wherein the induced dormancy is released by chilling the seeds at 2° C. to 10° C. in moisture for 4 to 40 days.

12. The method of claim 11 wherein the chilling is carried out at 5° C.

13. The method of claim 9 wherein the induced dormancy is released by application to the dormant seeds of a gibberellin.

14. The method of claim 13 wherein the gibberellin consists of from about 40% to 60% by weight gibberellin $A_7$ and from about 40% to 60% by weight gibberellin $A_4$.

15. A method of inducing releasable dormancy in non-dormant plant seeds for which gibberellin synthesis is necessary for germination, comprising the steps of
   (a) soaking said seeds in a solution of gibberellin synthesis inhibitor of concentration such and at a temperature such and for a time such as to induce dormancy therein, said gibberellin synthesis inhibitor being selected from the group consisting of tetcyclacis and paclobutrazol,
   (b) washing to remove the gibberellin synthesis inhibitor from the seeds, and
   (c) drying the seeds to their weight prior to soaking in step (a).

16. A method for postponing the germinability of plant seeds for which gibberellin synthesis is necessary, said method comprising the steps of inducing dormancy in said seeds by the method of claim 15, and after a desired interval releasing the induced dormancy.

17. The method of claim 22 wherein the plant seeds are selected from the group consisting of lettuce, tomato, pepper, carrot, onion, impatients and primrose seeds, and wherein the conditions of inducing dormancy include a temperature ranging from about 25° C. to 35° C. and a time of soaking in solution of gibberellin synthesis inhibitor of at least about 24 hours.

18. The method of claim 17 wherein the induced dormancy is released by soaking the seeds in water in light at about 25° C. to 35° C. for a time sufficient to release the induced dormancy.

19. The method of claim 17 wherein the induced dormancy is released by chilling the seeds at 2° C. to 10° C. in moisture for 4 to 15 days.

20. The method of claim 19 wherein the chilling is carried out at 5° C.

21. The method of claim 17 wherein the induced dormancy is released by application to the dormant seeds of a gibberellin.

22. The method of claim 21 wherein the gibberellin consists of from about 40% to 60% by weight gibberellin $A_7$ and from about 40% to 60% by weight gibberellin A4.

23. The method of claim 22 wherein the plant seeds are lettuce seeds.

* * * * *